United States Patent [19]

Lee

[11] 4,312,925

[45] Jan. 26, 1982

[54] METHOD OF MANUFACTURING THE BURN AND FROSTBITE PLASTER

[76] Inventor: Bae Y. Lee, #271 Ma-Chun Dong, Gang Nam Ku, Seoul, Rep. of Korea

[21] Appl. No.: 67,085

[22] Filed: Oct. 23, 1979

[51] Int. Cl.³ .............................................. B32B 9/00
[52] U.S. Cl. ..................................... 428/484; 424/28; 424/38; 424/DIG. 13; 428/486; 428/688; 428/702
[58] Field of Search ................. 424/28, 145, 156, 165, 424/194, 196, 363, DIG. 13, 38; 428/484, 497, 539, 486, 688, 702

[56] References Cited

U.S. PATENT DOCUMENTS

| | | | |
|---|---|---|---|
| 2,563,593 | 8/1951 | Engel | 424/28 |
| 2,579,367 | 12/1951 | Curtis et al. | 424/28 |
| 2,700,636 | 1/1955 | Ashton | 424/28 |
| 3,419,006 | 12/1968 | King | 424/28 X |
| 3,943,248 | 3/1976 | Shulman | 424/DIG. 13 |

*Primary Examiner*—Marion Mc Camish

[57] ABSTRACT

This invention, improved the means of making the ointment or the emulsion and others which traditionally used for Burn and Frostbite, is for a new method of making the burn and frostbite plaster and it provides with the most safety.

1 Claim, No Drawings

METHOD OF MANUFACTURING THE BURN AND FROSTBITE PLASTER

It, by mixing Paraffine, Resin, Precipitated Calcium Carbonate, Fluid Paraffine, is a method softening the mixtures to 38°-42° C. by the automatic reducing mixer. The traditional medicinal water used for Burn and Frostbite, as a relaxant to the affected part of about 1 degree, were made in a single ointment of sebaceous oil, Ranotine, Vaseline, Gliseline, Zinc Oil, Zinc Vaseline etc., and in order to prevent 2nd infection of the affected part, Vaseline Guarze or Prusine Guarze was being used for curing the injuries by covering the affected part. The ointment of fluids made by such method may relieve some pains and tensions caused by minor injuries of 1 degree, but had little effect to cover 2 degree injuries or 2nd infection. It is because the customary ointment and fluids are lack of distinctive features, in the processing, such as inflammation-relief, anodyne, sterrilization, effete matter evacuation etc. in the medications and these features are very difficult in treating such injuries, though a composite medicine has really been required for the said medicinal features.

In this invention, developed a new method for plaster of Burn and Frostbite in the result of resolving the pertinent difficulties.

The followings are details of the making method:

Hardened Paraffine Plaster is made by mixing Paraffine-2%, Zinc Oxide-1.5%, Fat Acid-0.5%, Pine Resin-0.3%, Rubber-0.6%, Precipitated Calcium Carbonate-3.1%, Liquid Paraffine-2% (Weight Rate), and the hardened Paraffine Plaster-10% is mixed with Resin-3%, Precipitated Calcium Carbonate-52%, Paraffine Liquid-35% (Weight Rate), then soften for 2-3 hours at less one time mixing rotation per second at the temperature 38°-42° C. by using Automatic Reducing Mixer, and then if required, other key chemicals may be added. This drugs are to be spreaded on oil-paper and vinyl for use.

This product is suitable for use by spreading it on oil-paper and vinyl as it can be adhered under 36°-42° C., and after adhered on skin 24 hours later, being removed cleanly from skin and leave nothing on skin. And this product expand skin capillary and assimilated rapidly, and at the same time it is made to not only maintain the effective medication function of inflammation-relief, anodyne, sterilization, effete-matter evacuation and congestion for 24 hours but also not deteriorate the quality when stored according to the storage regulations. And the properties and effectiveness of this product are not obvious all-together, for there are differences in combination rate, mixing and combination of the principle material and in processing speed, and in increase of the adhesive power and tension caused by physical variation of the composition—that is, density of molecules. Practical Example:

Mixing Paraffine-200 g, Zinc Oxide-150 g, Fat Acid-50 g, Pine Resin-30 g, Rubber (Raw)-60 g, Precipitated Calcium Carbonate-310 g, Paraffine Liquid-200 g and make a hardened Paraffine Plaster, and mix 100% of the hardened Paraffine Plaster with Resin-30%, Precipitated Calcium Carbonate-520%, Paraffine Liquid-350% and by Automatic Reducing Mixer, soften the mixture at less one time mixing rotation per second at 38°-42° C. for 2-3 hours to be 1,000 g product. And to this product mix or combine with the key medicinal material and then optionally spread on oil-paper and vinyl for use.

Method of Experiment(Test)

(1) The result of test, in compliance with Item-32 and Item-33 of the general test of Pharmacy Code, for the melting point and coagulating point of this product showed the melting and coagulating temperatures to be under 38°-42° C.

(2) When this product was dressed on skin for testing purpose, showed a distinctive medicinal function of inflammation-relief, anodyne, sterilization, effete-matter evacuation, congestion on the affected part.

(3) When this product is stored according to the regulation, no deterioration of quality and no loss of adhesive has been confirmed.

I claim:

1. The method of forming a plaster for Burns and Frostbite which can be applied directly on the affected part or wounds comprising mixing a hardened Paraffine Plaster (100% by weight) which comprises Paraffine (10%), Zinc Oxide (15%), Fat Acid (5%), Pine Resin (3%), Raw Rubber (6%), Precipitated Calcium Carbonate (51%) and Liquid Paraffine (10%) with a mixture of Resin (3%), Precipitated Calcium Carbonate (37%), Liquid Paraffine (30%) and Paraffine (15%) by letting the mixtures soften for 2 to 3 hours at a mixing rate of less than one rotation speed per second at 38 C. to 42 C. and then spreading this mixture after it's being added with a key chemical on oil paper or vinyl sheeting.

* * * * *